United States Patent
Squire et al.

(10) Patent No.: US 7,066,905 B2
(45) Date of Patent: Jun. 27, 2006

(54) METHOD AND APPARATUS FOR ACCURATE POSITIONING OF A DUAL BALLOON CATHETER

(76) Inventors: James C. Squire, 1949 Mountain View Rd., Buena Vista, VA (US) 24416; Elazer R. Edelman, 30 Warren St., Brookline, MA (US) 02445; Paul Tierstein, 1515 Coast Wallz, La Jolla, CA (US) 92037

( * ) Notice: Subject to any disclaimer, the term of this patent is extended or adjusted under 35 U.S.C. 154(b) by 500 days.

(21) Appl. No.: 10/293,002

(22) Filed: Nov. 13, 2002

(65) Prior Publication Data

US 2004/0092870 A1    May 13, 2004

(51) Int. Cl.
*A61M 31/00* (2006.01)
*A61M 29/00* (2006.01)

(52) U.S. Cl. .................... 604/103.08; 604/101.04; 604/103.06

(58) Field of Classification Search ............. 604/96.01, 604/101.01, 101.02, 101.04, 101.05, 103.03, 604/103.06, 103.08
See application file for complete search history.

(56) References Cited

U.S. PATENT DOCUMENTS

| | | | | |
|---|---|---|---|---|
| 4,655,746 A | * | 4/1987 | Daniels et al. | 604/509 |
| 4,927,412 A | * | 5/1990 | Menasche | 604/103.08 |
| 5,024,658 A | * | 6/1991 | Kozlov et al. | 604/101.04 |
| 5,370,653 A | * | 12/1994 | Cragg | 606/170 |
| 5,423,745 A | * | 6/1995 | Todd et al. | 604/500 |
| 5,462,529 A | * | 10/1995 | Simpson et al. | 604/101.04 |
| 5,653,690 A | * | 8/1997 | Booth et al. | 604/103.07 |
| 5,720,726 A | * | 2/1998 | Marcadis et al. | 604/103.08 |
| 5,795,331 A | * | 8/1998 | Cragg et al. | 604/103.01 |
| 5,971,954 A | * | 10/1999 | Conway et al. | 604/101.05 |
| 6,176,851 B1 | * | 1/2001 | Tsugita et al. | 604/509 |
| 6,540,719 B1 | * | 4/2003 | Bigus et al. | 604/96.01 |
| 6,663,589 B1 | * | 12/2003 | Halevy | 604/96.01 |
| 2002/0010418 A1 | * | 1/2002 | Lary et al. | 604/101.04 |
| 2002/0026145 A1 | * | 2/2002 | Bagaoisan et al. | 604/96.01 |
| 2003/0055483 A1 | * | 3/2003 | Gumm | 623/1.11 |
| 2004/0064092 A1 | * | 4/2004 | Tsugita et al. | 604/101.04 |
| 2005/0124843 A1 | * | 6/2005 | Singh | 600/3 |

* cited by examiner

*Primary Examiner*—Sharon Kennedy
(74) *Attorney, Agent, or Firm*—Bell, Boyd & Lloyd PLLC

(57) ABSTRACT

Embodiments of the present invention are directed to a method and apparatus for accurate positioning of a dual balloon catheter. In one embodiment of the present invention, a first balloon provides an anchoring point. In one embodiment, the first balloon has protrusions to help secure its position. In one embodiment, once the first balloon is inflated, it provides a fixed position relative to which a second balloon is accurately positioned in the treatment region. In another embodiment, a second balloon imparts a radial force. In another embodiment, a second balloon imparts an axial force, using the first balloon as an anchor against which the force is applied. The force may be applied in a forward or a backward direction. In yet another embodiment, a second balloon imparts a rotational force, using the first balloon as an anchor against which the force is applied.

20 Claims, 7 Drawing Sheets

METHOD AND APPARATUS FOR ACCURATE POSITIONING OF A DUAL BALLOON CATHETER

BACKGROUND OF THE INVENTION

1. Field of the Invention

The present invention relates to the field of balloon catheters, and in particular to a method and apparatus for accurate positioning of a dual balloon catheter.

2. Background Art

Balloon catheters are frequently used to impart axial or radial force to the interior of vessels in the body. However, prior art balloon catheters are difficult to initially position precisely, and precise positioning can be difficult to maintain as radial or axial forces are applied. Further, it is frequently impossible, due to the flexible nature of the catheter, to impart axial forces in more than one direction. This problem can be better understood by a review of balloon catheters.

Balloon Catheters

Balloon catheters are used for a variety of medical treatments. The ability to feed the flexible catheter through vessels in the body and, then, inflate a balloon portion of the catheter provides medical practitioners with the ability to impart radial or axial force from within a vessel of the body. Balloon catheters are frequently used to place stents. Another frequent use is to shear away obstructions from vessel walls (e.g. plaque on artery walls). Yet another use of balloon catheters is to enclose a region of a vessel between two balloons of the catheter and, then, introduce a treatment fluid into the enclosed region. Still another use is removing kidney stones by expanding the uterine wall and enabling the stone to move more readily out of the body.

Prior art balloon catheters share a common drawback: their accuracy is limited by the elasticity of the artery and its supporting structures. Since the artery and support structure can typically stretch up to 10% longitudinally, it is difficult to accurately place a balloon. It is especially difficult when attempting to position a balloon in a one millimeter long region using a one meter catheter (typical dimensions in some procedures).

Prior art balloon catheters are also prone to "watermelon seeding", a type of positioning error commonly seen when dilating in-stent restenosis. This error occurs when a partially expanded balloon slips forcefully in the axial direction through the stationary embedded stent, similar to the manner in which a watermelon seed can be launched between pressed fingers.

A further drawback of balloon catheters is encountered when attempting to apply axial force. Prior art balloon catheters can only exert axial shearing forces when pulled in a retrograde fashion. This limitation is due to the fact that the flexible catheter system buckles when pushed. Thus, a balloon catheter is analogous to a string attached to a weight. The string can exert a force on a weight when pulled but not when pushed.

Prior Art Balloon Catheters

An example of a prior art balloon catheter is found in U.S. Pat. No. 4,295,464 issued to Shihata. The patent is directed to a catheter for removing ureteral stones having two treatment balloons. A first treatment balloon is positioned and inflated to provide increasing outward radial force to the inner walls of the ureter immediately below the position of the arrested stone. This expands the inner walls to the extent that the diameter between the walls at that point is larger than the diameter of the stone. The second treatment balloon is inflated and imparts a downward (retrograde) pressure to dislodge the stone. However, because both balloons are used as treatment balloons, the efficiency of the device suffers from the same precise position problem common to other balloon catheters. Additionally, the device is unable to impart axial sheering force in anything other than a retrograde direction.

Another example of a prior art balloon catheter is found in U.S. Pat. No. 5,074,845 issued to Miraki. The patent is directed to a catheter having a balloon that has an anchoring portion, a waste and a dilation portion. The waste is formed by heat treating a portion of the balloon so that the waste separates the anchoring portion from the dilation portion. The balloon is positioned near an occlusion and inflated so that the anchoring portion immobilizes the balloon. Then, the dilation portion extends through the occlusion site as the balloon inflates and eventually dilates the occluded area. However, the anchoring portion of the balloon must still be precisely positioned, so the catheter suffers from the same precise position problem common to other balloon catheters. Additionally, the device is unable to impart axial sheering force.

A similar balloon catheter is described in U.S. Pat. No. 5,458,573 issued to Summers and directed to a catheter with two treatment balloons. The first balloon is used to impart radial force upon a treatment area. The second balloon is smaller than the first balloon and is used to widen narrow treatment areas so that the catheter and first balloon may he advanced. The second balloon may also be used to trap freed obstructions (e.g., a loosened blood clot) during extraction of the catheter by keeping the second balloon inflated during extraction. This catheter also has the positioning and axial force limitations common to prior art balloon catheters.

Another similar balloon catheter is found in U.S. Pat. No. 4,990,139 issued to Jang and directed to a catheter with two treatment balloons. The first balloon is used to impart radial force upon a treatment area. The second balloon is larger than the first balloon and is used to widen the treatment area further. Similarly, a third, even larger balloon could be used. However, the additional treatment balloons do not eliminate or reduce the positioning and axial force limitations common to prior art balloon catheters.

Another balloon catheter is described in U.S. Pat. No. 5,788,708 issued to Hegde and directed to a catheter with multiple treatment balloons. The balloons are used to dilate vessel walls and place stents without the use of multiple, single balloon catheters._However, the additional treatment balloons do not eliminate or reduce the positioning and axial force limitations common to prior art balloon catheters.

A similar balloon catheter is found in U.S. Pat. No. 5,320,605 issued to Sahota is directed to a catheter with multiple treatment balloons. The balloons are at a fixed distance from each other and may be operated independently. The use of multiple smaller treatment balloons rather than a single, long treatment balloon enables the catheter to treat areas that are not easily accessible by single balloon catheters. While the multiple treatment balloons make maneuvering through turns in a vessel more efficient, they do not eliminate or reduce the positioning and axial force limitations common to prior art balloon catheters.

Yet another example of a prior art balloon catheter is found in U.S. Pat. No. 5,423,745 issued to Todd. The patent is directed to a catheter for introducing liquid into a body passageway. The catheter of Todd has an immobilizing balloon, which may have retention enhancements such as protruberances. Additionally, the catheter of Todd also has a sealing balloon used to enclose a portion of the body passageway between the immobilizing balloon and the sealing balloon. However, the catheter is subject to the same positioning and axial force limitations common to other balloon catheters.

A similar balloon catheter is described in U.S. Pat. No. 5,919,163 issued to Glickman and directed to a catheter for creating an operating area within a body passageway. The catheter of Glickman has two sealing balloons, and an operating area is formed between the balloons upon inflation. Fluid may be introduced to the operating area, and the distance between the balloons is adjustable. However, the catheter is subject to the same positioning and axial force limitations common to other balloon catheters.

Additional similar balloon catheters are found in U.S. Pat. No. 4,911,163 issued to Fina, U.S. Pat. No. 5,342,306 issued to Don Michael, U.S. Pat. No. 4,445,892 issued to Hussein, all being directed to catheters for creating an operating area within a body passageway. The catheters of the patents have two sealing balloons, and an operating area is formed between the balloons upon inflation. Fluid may be introduced to the operating area, and if an obstruction is dislodged by the treatment, one or both of the balloons can be maintained as inflated during withdrawal of the catheter to aid in extracting the dislodged obstruction. However, the catheters are subject to the same positioning and axial force limitations common to other balloon catheters.

More balloon catheters are described in U.S. Pat. No. 6,156,005 and U.S. Pat. No. 5,423,742, both issued to Theron and directed to catheters having an occlusion balloon and a treatment balloon. The occlusion balloon is inflated to prevent fragments from escaping during treatment. The treatment balloon is inflated to dilate a treatment stent. However, the catheters are subject to the same positioning and axial force limitations common to other balloon catheters.

Still another balloon catheter is described in U.S. Pat. No. 5,868,708 issued to Hart and directed to a catheter having a balloon that can be inflated into predetermined configurations. A mesh around the balloon controls the configuration of the inflated balloon. However, the catheter is subject to the same positioning and axial force limitations common to other balloon catheters.

Additional balloon catheters are found in U.S. Pat. No. 5,653,690 issued to Booth, U.S. Pat. No. 5,487,730 and U.S. Pat. No. 5,720,726 issued to Marcadis, and U.S. Pat. No. 4,927,412 issued to Menasche, all directed to catheters for introducing liquid into the heart having a single retention (or immobilizing) balloon. The retention balloon can have retention enhancements such as sloping spikes or barbed protrusions. However, the catheters are subject to the same positioning and axial force limitations common to other balloon catheters.

Another balloon catheter is found in U.S. Pat. No. 3,448,739 issued to Stark and directed to a catheter having a single balloon. The balloon may be used either as an occlusion balloon during introduction of fluids through the catheter or as a treatment balloon used to impart radial force against a passage wall. However, the catheter is subject to the same positioning and axial force limitations common to other balloon catheters.

Still another balloon catheter is described in U.S. Pat. No. 6,258,099 B1 issued to Mareiro and directed to a catheter having a single balloon. The balloon has protrusions to prevent unwanted movement of an expandable, implantable medical device such as a stent during delivery and deployment. However, the catheter is subject to the same positioning and axial force limitations common to other balloon catheters.

Yet another balloon catheter is described in U.S. Pat. No. 5,019,075 issued to Spears and directed to a catheter having a single balloon. A heated fluid is pumped through the balloon upon inflation to create a smooth channel upon deflation to reduce abrupt arterial closure or gradual restenosis. However, the catheter is subject to the same positioning and axial force limitations common to other balloon catheters.

Another balloon catheter is found in U.S. Pat. No. 5,968,012 issued to Ren and directed to a catheter having a single balloon. The catheter has a length compensator to compensate for balloon movement. However, the catheter is subject to the same positioning and axial force limitations common to other balloon catheters.

Still another balloon catheter is described in U.S. Pat. No. 5,868,703 issued to Bertolero and directed to a catheter having a single balloon. Channels in the catheter enable delivery of blood and other fluids during treatment or cardiac surgery. The balloon has protrusions to help secure its position. However, the catheter is subject to the same positioning and axial force limitations common to other balloon catheters.

Yet another balloon catheter is described in U.S. Pat. No. 5,179,961 issued to Littleford is directed to a catheter having a positioning balloon. The positioning balloon is inflated to center the catheter as it is maneuvered through winding and potentially occluded passageways. When the catheter is centered, it is less likely to become stuck. However, the catheter is subject to the same positioning and axial force limitations common to other balloon catheters.

Further examples of balloon catheters are described in U.S. Pat. No. 5,616,149 issued to Barath (directed to a catheter with a treatment balloon having cutting edges for making lateral cuts in the vessel wall); U.S. Pat. No. 5,693,014 and U.S. Pat. No. 5,746,745, both issued to Abele (directed to an angioplasty balloon wherein when not inflated, the balloon surface has a low coefficient of friction, but, when the balloon is inflated, a second surface is exposed that has a higher coefficient of friction); U.S. Pat. No. 4,292,974 issued to Fogarty (directed to a catheter with a treatment balloon, wherein the balloon is twisted when not inflated so as to enable the balloon to fit into smaller spaces); U.S. Pat. No. 4,351,341 issued to Goldberg (directed to a catheter having a lumen formed from a coil); U.S. Pat. No. 5,250,070 issued to Parodi (directed to an angioplasty balloon, wherein the balloon is irregularly formed, having a plurality of grooves and radially projecting parts between the grooves, and wherein the balloon is used to impart radial force to a treatment area in a less traumatic manner than other designs); U.S. Pat. No. 6,018,857 issued to Duffy (directed to a method and apparatus for mounting a stent onto a catheter balloon); and U.S. Pat. No. 4,733,665 issued to Palmaz (directed to an expandable intraluminal vascular graft, wherein the graft is expanded using a catheter balloon). However, all of these catheters are subject to the same positioning and axial force limitations common to other balloon catheters.

SUMMARY OF THE INVENTION

Embodiments of the present invention are directed to a method and apparatus for accurate positioning of a dual balloon catheter. In one embodiment of the present invention, a first balloon provides an anchoring point. In one embodiment, the first balloon has protrusions to help secure its position. In one embodiment, once the first balloon is inflated, it provides a fixed position relative to which a second balloon is accurately positioned in the treatment region.

In another embodiment, a second balloon imparts a radial force. In another embodiment, a second balloon imparts an axial force, using the first balloon as an anchor against which the force is applied. The force may be applied in a forward or a backward (i.e., retrograde) direction.

In yet another embodiment, a second balloon imparts a rotational force, using the first balloon as an anchor against which the force is applied. In one embodiment, the second balloon has protrusions designed to assist in shearing away obstructions from vessel walls. In still another embodiment, a third balloon is used to isolate the treatment region from other portions of the vessel.

BRIEF DESCRIPTION OF THE DRAWINGS

These and other features, aspects and advantages of the present invention will become better understood with regard to the following description, appended claims and accompanying drawings where:

DETAILED DESCRIPTION OF THE INVENTION

The invention is a method and apparatus for accurate positioning of a dual balloon catheter. In the following description, numerous specific details are set forth to provide a more thorough description of embodiments of the invention. It is apparent, however, to one skilled in the art, that the invention may be practiced without these specific details. In other instances, well known features have not been described in detail so as not to obscure the invention.

Catheter With Anchoring Balloon and Treatment Balloon

In one embodiment, a catheter has two or more balloons and is capable of precise positioning. The catheter is also able to impart radial, axial and/or rotational shearing forces to a vessel wall. The catheter employs at least two balloons in a coaxial arrangement. In one embodiment of the present invention, a first balloon provides an anchoring point. In one embodiment, the first balloon has protrusions to help secure its position. A second balloon is used for treatment purposes.

Figure 1:
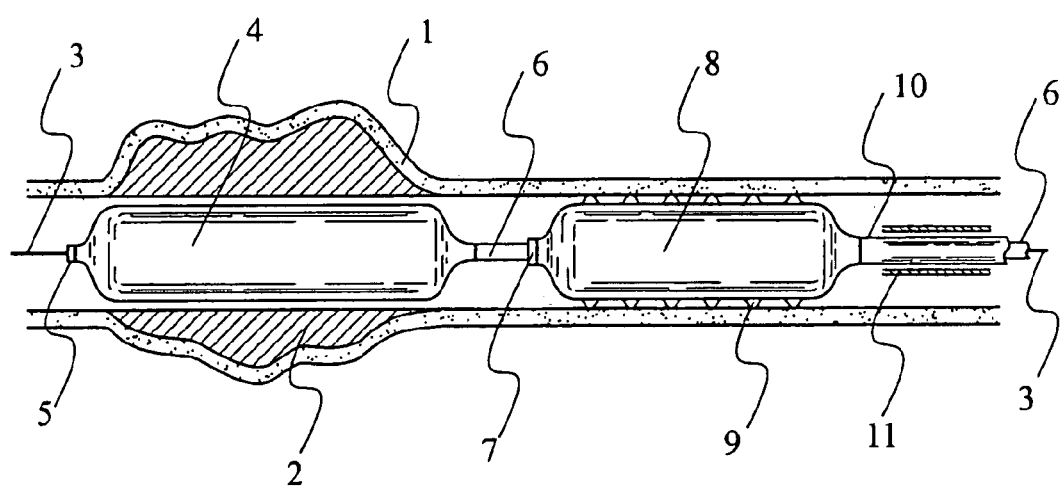
FIG. 1 is a block diagram of a cross section of a dual balloon catheter in accordance with one embodiment of the present invention.

FIG. 1 illustrates a cross section of a dual balloon catheter in accordance with one embodiment of the present invention. A vessel 1 carrying body fluid is diseased, causing a partial or total occlusion 2. The dual balloon catheter is comprised of an inner catheter 6 with a distal treatment balloon 4 and a coaxially-mounted outer catheter 10 with a distal immobilizing (anchoring) balloon 8 preferably mounted proximally to the treatment balloon. In one embodiment, the immobilizing balloon has protrusions 9. In various embodiments, the treatment balloon is used either to expand an endovascular stent or is used as an angioplasty balloon to directly expand the diseased vessel.

The immobilizing balloon, when inflated, secures itself to the vessel and provides a stable platform against which the treatment balloon may be axially advanced or retracted with respect to the vascular occlusion. A central lumen 5 exists along the length of the inner treatment catheter that maybe used, in various embodiments, to accept a guide wire 3 or optionally an occlusion balloon to prevent retrograde blood flow during catheter exchanges. The guide wire is used to position the distal opening of the guide catheter 11 to a location just proximal of the occlusion. In one embodiment, treatment fluid is injectable between the immobilizing balloon and treatment balloon through the end 7 of the outer catheter.

Figure 2:
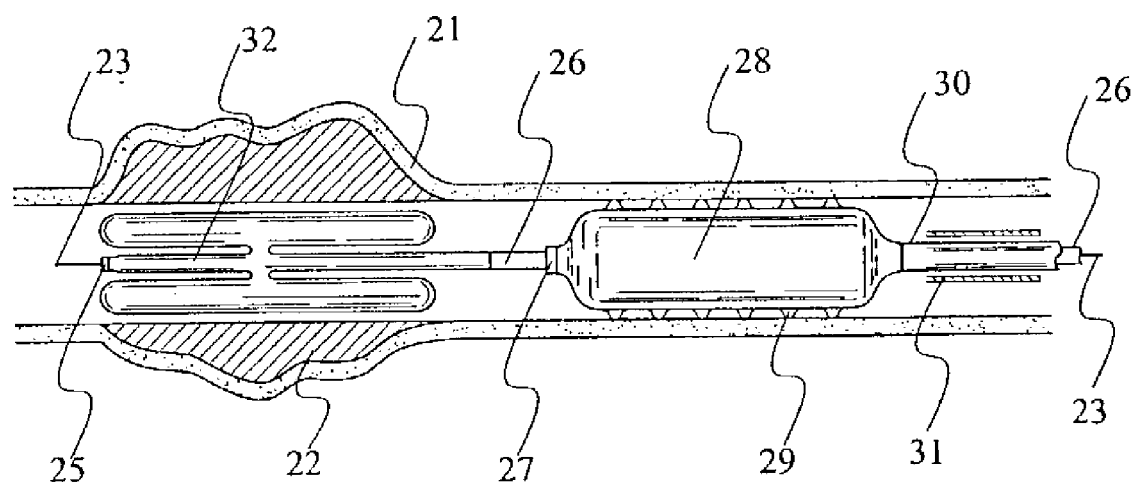
FIG. 2 is a block diagram of a cross section of a dual balloon catheter with a different treatment balloon from that of FIG. 1 in accordance with one embodiment of the present invention.

FIG. 2 illustrates a cross section of a dual balloon catheter with a different treatment balloon from that of FIG. 1 in accordance with one embodiment of the present invention. A vessel 21 carrying body fluid is diseased, causing a partial or total occlusion 22. The dual balloon catheter is comprised of an inner catheter 26 with a distal treatment balloon 32 and a coaxially-mounted outer catheter 30 with a distal immobilizing (anchoring) balloon 28 preferably mounted proximally to the treatment balloon. In one embodiment, the immobilizing balloon has protrusions 29. In various embodiments, the treatment balloon is used either to expand an endovascular stent or is used as an angioplasty balloon to directly expand the diseased vessel.

The immobilizing balloon, when inflated, secures itself to the vessel and provides a stable platform against which the treatment balloon may be axially advanced or retracted with respect to the vascular occlusion. A central lumen 25 exists along the length of the inner treatment catheter that maybe used, in various embodiments, to accept a guide wire 23 or optionally an occlusion balloon to prevent retrograde blood flow during catheter exchanges. The guide wire is used to position the distal opening of the guide catheter 31 to a location just proximal of the occlusion. In one embodiment, treatment fluid is injectable between the immobilizing balloon and treatment balloon through the end 27 of the outer catheter.

Positioning and Applying Force Using Dual Balloon Catheter

Various embodiments are used for a variety of applications including treatment of atherosclerotic lesions with focal expansion-resistant sites, precise endovascular stent placement, and expansion of specific sites along stents that were not fully deployed. In one embodiment, fixed (anchoring) balloon is first expanded within the vessel proximal to stenotic site, and provides a fixed platform against which axial force may be applied to position the proximally-placed movable balloon (i.e., the second balloon). Dual coaxial catheter sheaths permit precise positioning in a similar manner as a bicycle hand brake's coaxial cables enable precise and forceful positioning of the brake caliper through a considerable distance of flexible cable. Thus, embodiments of the present invention need not rely on the stiffness of the elastic artery and its supporting structures to provide a platform against which axial shearing forces are resisted.

Additionally, the positioning accuracy of various embodiments is not limited by changes in the length of the elastic blood vessel or duct.

In one embodiment, a guide wire is initially emplaced through an inguinal incision in the patient and is threaded under angiographic guidance to the site of vessel occlusion, often in the coronary or carotid arteries. The guide wire is used to position the distal opening of the guide catheter to a location just proximal of the occlusion. Then, the treatment balloon is placed inside the guide catheter and pushed into the center of the occluded region. In one embodiment, the treatment balloon is surrounded by an endovascular stent which is expanded and left as a permanent scaffold to reinforce the vessel walls. In another embodiment, the treatment balloon is used to stretch and displace the occluding material in an angioplasty procedure to restore vessel patency. After use, the treatment balloon is deflated and is withdrawn along with the guide wire and guide catheter.

In one embodiment, the immobilizing balloon catheter is constructed of a material that exhibits extremely little axial stretch, such as nylon-reinforced non-compliant polyurethane. In another embodiment, the immobilizing balloon is constructed of a material such as silicone rubber or compliant polyurethane that when expanded adheres well to the vascular surface. In one embodiment, this adherence is enhanced by the use of a multitude of nubs manufactured from an inflexible material such as high molecular weight polyvinyl that press into the vessel wall when the balloon is inflated and further inhibit axial displacement relative to the vessel wall.

In one embodiment, the guide wire and guide catheter are placed in the known manner. Then, the treatment balloon is placed, but not expanded. The immobilizing balloon is placed coaxially around the treatment balloon catheter and pushed forward until it is proximally adjacent to the treatment balloon. Then, the immobilizing balloon is inflated, and its dimensionally-stable catheter is used as a sleeve that transmits, without loss, any differential axial movement between the treatment and immobilizing catheters at the proximal end to the treatment balloon relative to the distal arterial wall. Because the treatment balloon catheter is coaxially mounted within the immobilizing balloon catheter and because the treatment immobilizing catheter is dimensionally stable, the only axially unsupported region of the treatment catheter is the few millimeters that separate the treatment and immobilizing balloons. In this embodiment, any axial displacement of the treatment balloon while it is inflated will impart axial shearing stress to the vessel wall.

In certain applications, it is preferred that no axial shear be imposed by the balloon (e.g., the region-selective expansion of an endovascular stent where axial shear may distort the stent or tear the balloon). The design of the embodiment illustrated in FIG. 2 permits axial repositioning of the treatment catheter while it is inflated without transmitting unwanted axial shearing stress to the vessel wall. In this embodiment, a flattened toroidally-shaped balloon is used that is capable of being rolled in its expanded state in a tank-tread fashion nearly half its length in either the proximal or distal directions. In one embodiment, the flattened toroid balloon is used to precisely position expandable endoluminal devices. In another embodiment, it is used to conduct angioplasty using a rapid reciprocating motion in concert with the immobilizing catheter.

Figure 3:
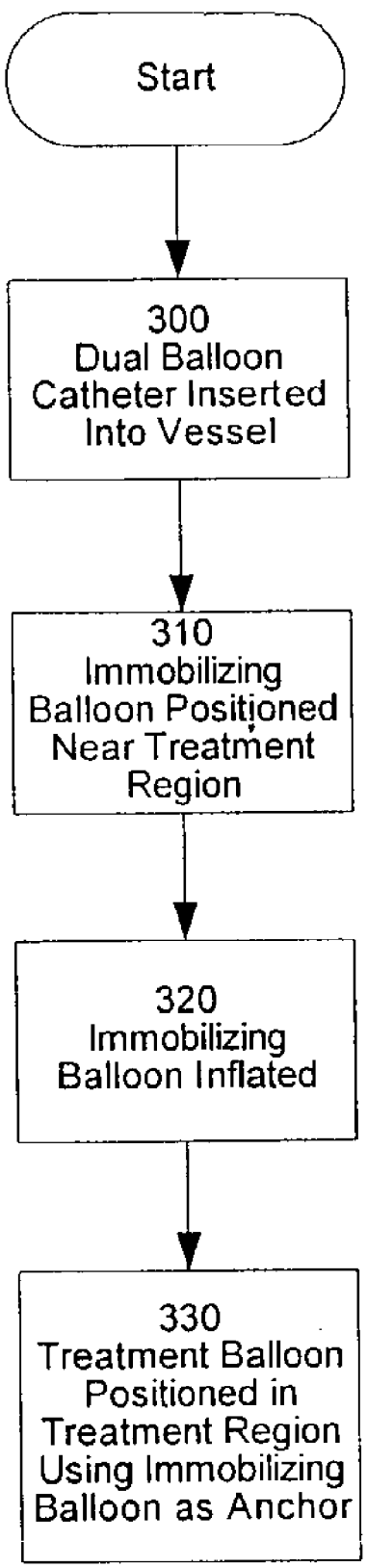
FIG. 3 is a flow diagram of the process of positioning a catheter treatment balloon in accordance with one embodiment of the present invention.

FIG. 3 illustrates the process of positioning a catheter treatment balloon in accordance with one embodiment of the present invention. At block 300, a dual balloon catheter is inserted into the vessel. At block 310, an immobilizing balloon is positioned near a treatment region. The immobilizing balloon is positioned such that it is not too close to the treatment region (i.e., so close to the region that the treatment balloon physically could not be positioned in the region because of any minimum separation between the two balloons). However, the immobilizing balloon is also positioned not too far from the treatment region (i.e., so far that the immobilizing balloon no longer has the desired anchoring effect). The exact boundaries for placement of the immobilizing balloon will vary depending upon the circumstances, but the range is sufficiently large to enable acceptable placement of the immobilizing balloon by one of ordinary skill in the art.

At block 320, the immobilizing balloon is inflated. At block 330, the treatment balloon is positioned in the treatment region, using the immobilizing balloon as an anchor. Because the treatment balloon is anchored proximally to the treatment area, less of the vessel can stretch. As a result, accurate placement of the treatment balloon is easier than with prior art techniques. Additionally, when the treatment balloon is inflated, the watermelon seeding problem is greatly reduced. This is because the immobilizing balloon maintains its position and the relative positions of the immobilizing balloon and the treatment balloon can be fixed during inflation of the treatment balloon. Thus, slippage of the treatment balloon (watermelon seeding) is less likely.

Radial Force

Figure 4:
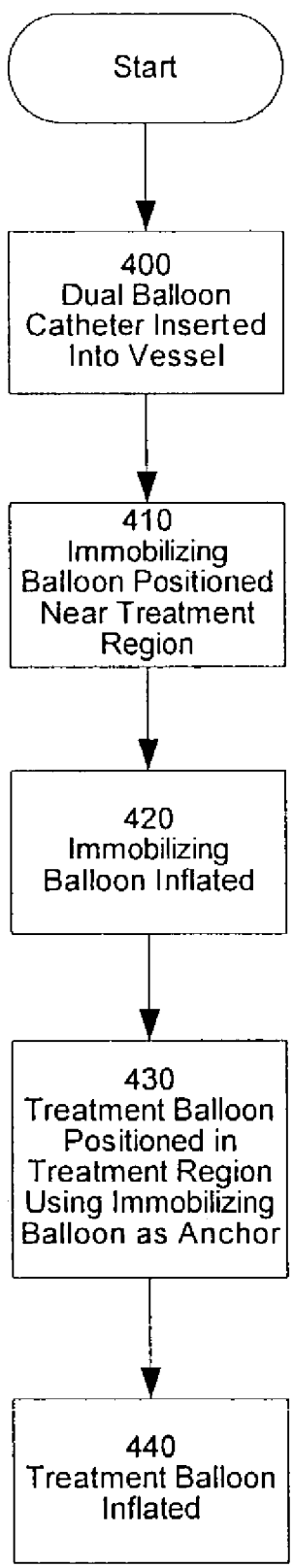
FIG. 4 is a flow diagram of the process of applying radial force with a treatment balloon in accordance with one embodiment of the present invention.

In one embodiment, the treatment balloon imparts a radial force. Thus, the treatment balloon can be used in angioplasty or stent placement. FIG. 4 illustrates the process of applying radial force with a treatment balloon in accordance with one embodiment of the present invention. At block 400, a dual balloon catheter is inserted into the vessel. At block 410, an immobilizing balloon is positioned near a treatment region. At block 420, the immobilizing balloon is inflated. At block 430, the treatment balloon is positioned in the treatment region, using the immobilizing balloon as an anchor. At block 440, the treatment balloon is inflated. Inflation of the treatment balloon imparts a radial force upon anything surrounding the treatment balloon (e.g., a vessel wall, an obstruction, or a stent).

Axial Force

Figure 5:
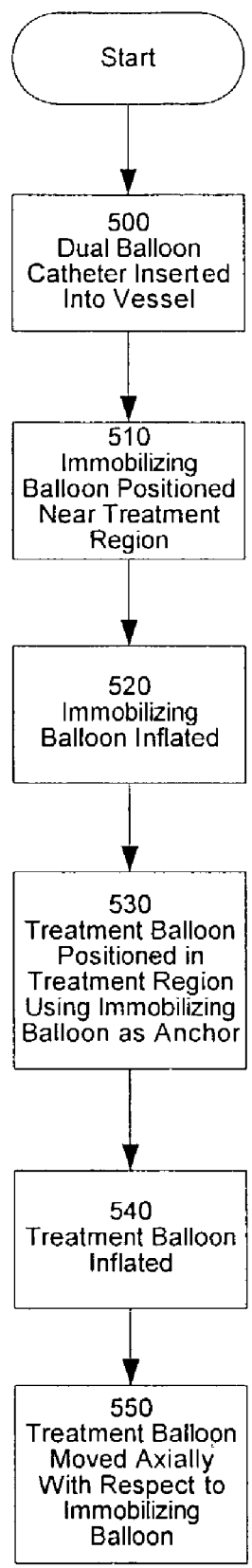
FIG. 5 is a flow diagram of the process of applying axial force in accordance with one embodiment of the present invention.

In another embodiment, a second balloon imparts an axial force, using the first balloon as an anchor against which the force is applied. The force may be applied in a forward or a backward (i.e. retrograde) direction. FIG. 5 illustrates the process of applying axial force in accordance with one embodiment of the present invention. At block 500, a dual balloon catheter is inserted into the vessel. At block 510, an immobilizing balloon is positioned near a treatment region. At block 520, the immobilizing balloon is inflated. At block 530, the treatment balloon is positioned in a desired location, using the immobilizing balloon as an anchor. At block 540, the treatment balloon is inflated.

Considered in long segments (e.g. the length of the catheter), the vasculature is flexible and can buckle. Conventional single-balloon catheters can provide axial shearing force in the retrograde direction by pulling a sufficient length of catheter away from the body to force the treatment balloon to overcome frictional resistance with the vessel wall, however because it must compress the entire length of vessel to do so it may slip over a longer distance than intended. Further, it is nearly impossible to push the balloon to impart a forward axial shearing force because the thin-walled catheter buckles inside the vessel, much as a string can be pulled but not pushed.

Considered in short segments (e.g., the distance between the immobilizing balloon and the treatment balloon), the vasculature is semi-rigid and can contract/expand only slightly. The treatment balloon in block 550 is positioned in close proximity to the treatment balloon, thus limiting the length of vessel in compression or expansion and enabling precise localization of the axial shear without risk of overshoot. Further, the dual coaxial sheaths enable substantial forward and retrograde axial shearing forces to be imparted without danger of buckling, much as the coaxial brake cable of a bicycle can provide substantial forces in both forward and retrograde directions relative to the fixed outer cable whereas the inner cable without the sheath, or with an outer sheath not fixed in position, can only be pulled.

Rotational Force

Figure 6:
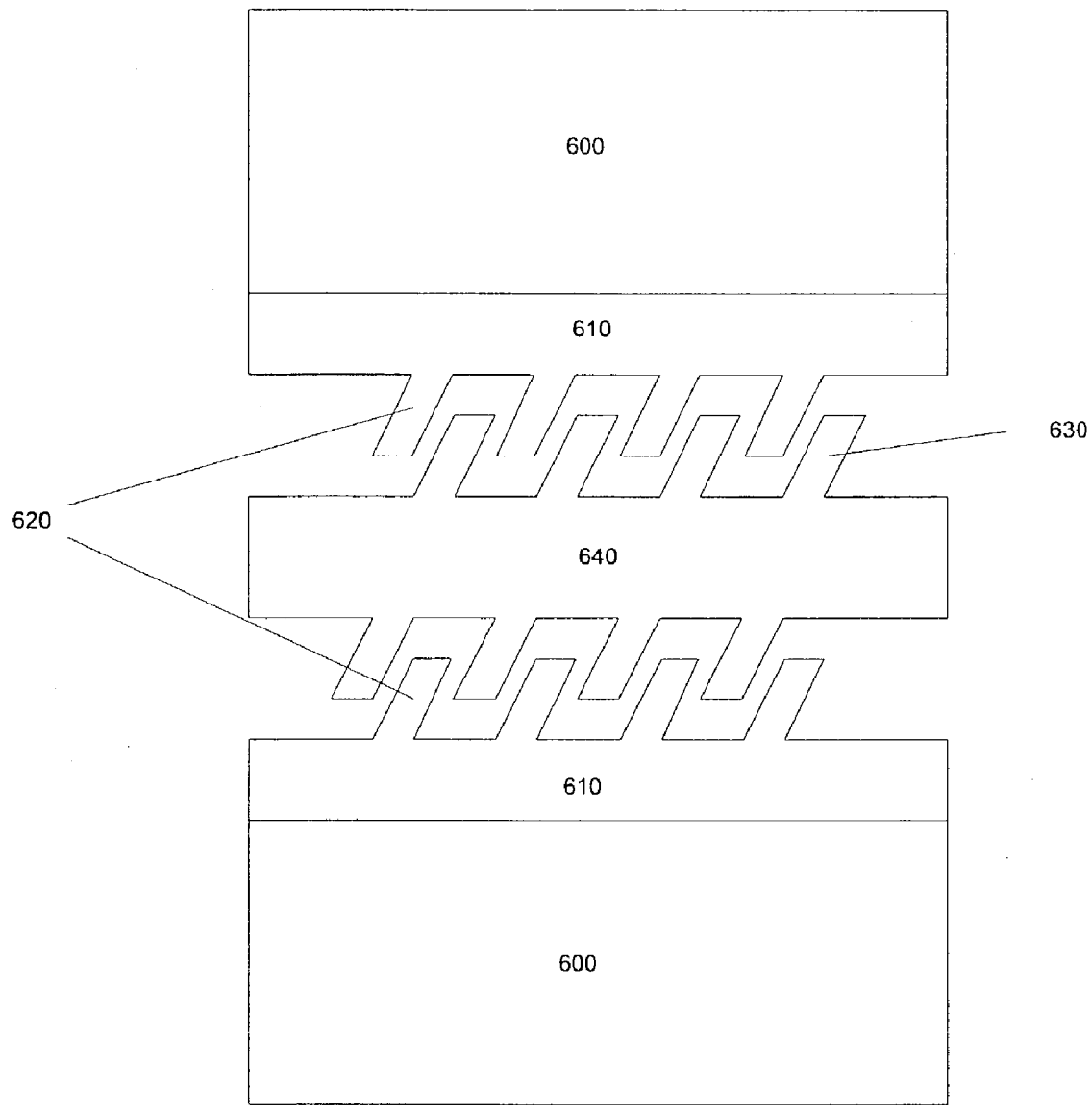
FIG. 6 is a block diagram of a cross section of a rotating treatment balloon in accordance with one embodiment of the present invention.

In yet another embodiment, a second balloon imparts a rotational force, using the first balloon as an anchor against which the force is applied. FIG. 6 illustrates a cross section of a rotating treatment balloon in accordance with one embodiment of the present invention. The treatment balloon 600 is on a sheath 610 which has threads 620. The threads are similar to the threads of a screw or bolt and are complemented by threads 630 on a rotation actuator 640. The rotation actuator can be moved axially independently of either the treatment balloon or the immobilizing balloon; however, typically the rotation actuator and treatment balloon move as one unit when rotation is not desired. A user causes the treatment balloon to rotate by moving the rotation actuator axially with respect to the treatment balloon. In other embodiments, other designs for rotation actuator are used wherein the designs enable the treatment balloon to be rotated with respect to the immobilizing balloon.

Figure 7:
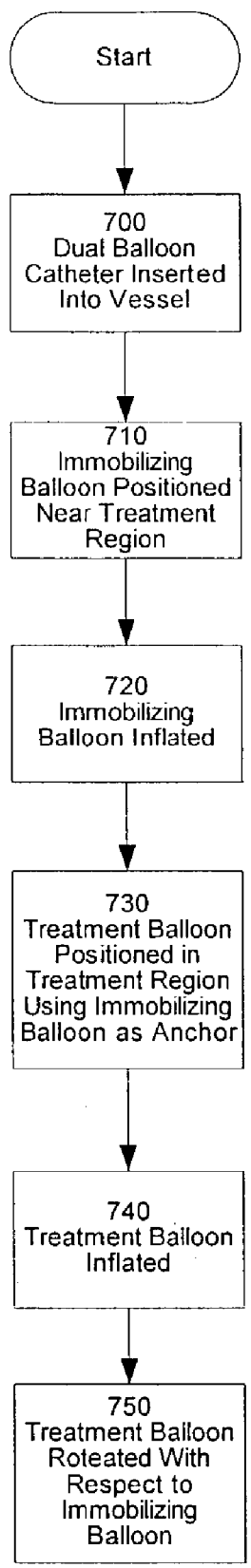
FIG. 7 is a flow diagram of the process of rotating a treatment balloon in accordance with one embodiment of the present invention.

FIG. 7 illustrates the process of rotating a treatment balloon in accordance with one embodiment of the present invention. At block 700, a dual balloon catheter is inserted into the vessel. At block 710, an immobilizing balloon is positioned near a treatment region. At block 720, the immobilizing balloon is inflated. At block 730, the treatment balloon is positioned in a desired location, using the immobilizing balloon as an anchor. At block 740, the treatment balloon is inflated. At block 750, the treatment balloon is rotated with respect to the immobilizing balloon.

Treatment Protrusions and Occlusion Balloons

In one embodiment, the treatment balloon has protrusions designed to assist in shearing away obstructions from vessel walls. In still another embodiment, a third (occlusion) balloon is used to isolate the treatment region from other portions of the vessel. The third balloon extends beyond the treatment balloon and, together with the immobilizing balloon, isolates the treatment region from the rest of the vessel. Thus, treatment solutions may be introduced into the region and obstructions removed from the region without contaminating other portions of the vessel.

In one embodiment, an occlusion balloon is threaded over the guide wire and through the occlusion site. The occlusion balloon is expanded before the treatment catheter. Thus, the occlusion balloon prevents retrograde blood flow if the proximal treatment balloon catheter is removed, for example to permit catheter exchanges allowing initial stent deployment with a compliant balloon and final stent expansion with a high-pressure, low-compliance balloon.

Descriptions of various embodiment have involved a catheter with two balloons, typically operating in a blood vessel. However, embodiments of the invention are not limited to only two balloon or to operation within blood vessels. Three or more balloons are used in various embodiments, and various embodiments are used in other lumens (e.g., the biliary duct or ureter).

Thus, a method and apparatus for accurate positioning of a dual balloon catheter is described in conjunction with one or more specific embodiments. The invention is defined by the following claims and their full scope and equivalents.

What is claimed is:

1. A method of using a treatment balloon comprising:
positioning an immobilizing balloon proximally to a treatment region, wherein when inflated, said immobilizing balloon maintains its position;
inflating said immobilizing balloon;
positioning said treatment balloon in a treatment region wherein said step of positioning is performed relative to said immobilizing balloon;
inflating said treatment balloon; and
rotating said treatment balloon relative to said immobilizing balloon.

2. The method of claim 1 wherein said immobilizing balloon has protrusions designed to enhance the ability of said immobilizing balloon to maintain its position.

3. The method of claim 1 wherein said treatment balloon imparts a radial force.

4. The method of claim 3 wherein said radial force is used in placing a stent.

5. The method of claim 3 wherein said radial force is used in angioplasty.

6. The method of claim 1 wherein said treatment balloon imparts an axial force.

7. The method of claim 6 wherein said axial force is not applied in a retrograde direction.

8. The method of claim 1 further comprising:
positioning an occlusion balloon; and
inflating said occlusion balloon.

9. The method of claim 1 wherein said treatment balloon has protrusions designed to increase the capability of said treatment balloon to shear away an occlusion.

10. The method of claim 1 wherein said occlusion balloon occludes a first end of said treatment region, and wherein said immobilizing balloon occludes a second end of said treatment region.

11. A catheter system comprising:
an immobilizing balloon, wherein when inflated, said immobilizing balloon maintains its position;
an immobilizing balloon positioning system configured to position said immobilizing balloon proximally to a treatment region;
a first inflation system configured to inflate said immobilizing balloon;
a treatment balloon;
a treatment balloon positioning system configured to position said treatment balloon, relative to said immobilizing balloon, in a treatment region; and
a second inflation system configured to inflate said treatment balloon, wherein said treatment balloon is configured to rotate relative to said immobilizing balloon.

12. The catheter system of claim 11 wherein said immobilizing balloon has protrusions designed to enhance the ability of said immobilizing balloon to maintain its position.

13. The catheter system of claim 11 wherein said treatment balloon is configured to impart a radial force.

14. The catheter system of claim 13 wherein said radial force is used in placing a stent.

15. The catheter system of claim 13 wherein said radial force is used in angioplasty.

16. The catheter system of claim 11 wherein said treatment balloon is configured to impart an axial force.

17. The catheter system of claim 16 wherein said axial force is not applied in a retrograde direction.

18. The catheter system of claim 11 further comprising:
an occlusion balloon;
an occlusion balloon positioning system configured to position said occlusion balloon such that said treatment balloon is between said immobilizing balloon and said occlusion balloon; and
a third inflation system configured to inflate said occlusion balloon.

19. The catheter system of claim 11 wherein said treatment balloon has protrusions designed to increase the capability of said treatment balloon to shear away an occlusion.

20. The catheter system of claim 18 wherein said occlusion balloon is adapted to occlude a first end of said treatment region, and wherein said immobilizing balloon is adapted to occlude a second end of said treatment region.

* * * * *

UNITED STATES PATENT AND TRADEMARK OFFICE
CERTIFICATE OF CORRECTION

PATENT NO.       : 7,066,905 B2                                                Page 1 of 1
APPLICATION NO.  : 10/293002
DATED            : June 27, 2006
INVENTOR(S)      : James C. Squire, Elazer R. Edelman and Paul Teirstein It is certified that error appears in the above-identified patent and that said Letters Patent is hereby corrected as shown below:

Item [75]
There are two errors in the issued patent:
   1) the name of the third inventor is Paul Teirstein, not Paul Tierstein
   2) his address is Coast Walk, not Coast Wallz Signed and Sealed this Fourteenth Day of November, 2006

JON W. DUDAS
*Director of the United States Patent and Trademark Office*